(12) United States Patent
Jiang

(10) Patent No.: US 7,078,488 B2
(45) Date of Patent: Jul. 18, 2006

(54) TEMPERATURE-STABLE GLYCOSYLATED RECOMBINANT CHICKEN CYSTATIN AND THE USE THEREOF

(75) Inventor: Shann-Tzong Jiang, St. Taipei (TW)

(73) Assignee: Nugen Bioscience (Taiwan) Co., Ltd., Taipei (TW)

( * ) Notice: Subject to any disclaimer, the term of this patent is extended or adjusted under 35 U.S.C. 154(b) by 324 days.

(21) Appl. No.: 10/628,629

(22) Filed: Jul. 28, 2003

(65) Prior Publication Data

US 2005/0026264 A1    Feb. 3, 2005

(51) Int. Cl.
 *C07K 1/00* (2006.01)
 *A23J 1/00* (2006.01)
 *A23J 1/02* (2006.01)
(52) U.S. Cl. ........................ 530/350; 426/656; 426/657
(58) Field of Classification Search ................ 530/350; 426/656, 657
See application file for complete search history.

(56) References Cited

OTHER PUBLICATIONS

Shann-Tzong Jiang, *Effect of Glycosylation Modification ($N$-$Q$-$^{108}I$→$N$-$O$-$^{108}T$) on the Freezing Stability of Recombinant Chicken Cystatin Overexpressed in Pichia pastoris X-33*, J. Agric. Food Chem., 2002, vol. 50, pp. 5313-5317.

*Primary Examiner*—Mark Navarro
(74) *Attorney, Agent, or Firm*—Scully, Scott, Murphy & Presser, P.C.

(57) ABSTRACT

The present invention relates to a N-glycosylation-modified recombinant chicken cystatin, characterized in that $Asn_{106}$-$Ile_{108}$ in its amino acid sequence is modified to $Asn_{106}$-$Thr_{108}$. The present invention also relates to a method for producing said N-glycosylation-modified recombinant chicken cystatin, wherein a site-directed mutated cDNA encoding chicken cystatin is cloned in an expression vector, with which a yeast strain is in turn transformed, and the yeast transformant is then cultured for producing a recombinant chicken cystatin wherein the Asn residue in the $Asn_{106}$-$Thr_{108}$ of its amino acid sequence that is produced by said site-directed mutagenesis can be modified by N-glycosylation. The N-glycosylation-modified recombinant chicken cystatin disclosed in the present invention has improved stability in a freezing-thawing process and in a heating process.

8 Claims, 4 Drawing Sheets

TEMPERATURE-STABLE GLYCOSYLATED RECOMBINANT CHICKEN CYSTATIN AND THE USE THEREOF

FIELD OF THE INVENTION

The present invention relates to the field of glycosylation of protein. Specifically, the present invention relates to glycosylation of chicken cystatin, wherein the chicken cystatin could be produced by genetic engineering technique. The glycosylated recombinant chicken cystatin of the present invention has improved stability to temperature.

BACKGROUND OF THE INVENTION

The cystatin superfamily includes a number of cysteine protease inhibitors that are widely distributed in tissues and body fluids of mammalians (6). Chicken cystatin, a well-studied cysteine protease inhibitor, is a small non-glycosylated protein having 116 amino acids linked with two disulphide bonds (1, 5, 6, 18, 34), which has been crystallized and subjected to the preliminary X-ray crystallographic studies (10, 11). Chicken cystatin is a reverse, tight-binding inhibitor of cysteine proteases such as papain and tissue protease B and L, and is considered to contribute to physiological control in which said proteases participate (7, 8, 9, 23, 24, 26, 31). Chicken cystatin inhibits the degradation of proteins in organisms and the softening of muscles of animals when said animals were dead. In food industries, for example, chicken cystatin is added to surimi for the inhibition of endogenous proteolysis of the surimi, thereby reducing the gel softening of said surimi.

However, it was found that chicken cystatin is stable to heat (18), but unstable to freezing or freeze-drying (1, 20). Application of chicken cystatin on the inhibition of autolysis or endogenous proteolysis was greatly restricted by its lower, unsatisfactory freezing tolerance. Especially, chicken cystatin, when added to surimi, is unstable and easily loses its activity in the freezing-thawing process of surimi. For expanding the use of the chicken cystatin in frozen products, the structure of chicken cystatin may need to be modified for increasing its flexibility and resistance to a freezing-thawing process.

Natural chicken cystatin is not a glycoprotein since there is no N-glycosylation site in its amino acid sequence. There was no teaching or suggestion in the art that change in one or more amino acid residues in the amino acid sequence of chicken cystatin could improve the stability of chicken cystatin to temperature. Further, there was no teaching or suggestion in the art that glycosylation of the changed amino acid residue(s) in the amino acid sequence of chicken cystatin could improve the stability of chicken cystatin to temperature.

The inventors of the present invention found that change in just an internal amino acid residue of chicken cystatin that is not located in its active site, i.e. $Asn_{106}$-$Ile_{108}$→$Asn_{106}$-$Thr_{108}$, by employing site-directed mutagenesis and genetic engineering technique without changing or destroying the stereo structure of the active site of chicken cystatin, could facilitate the glycosylation of said $Asn_{106}$, whereby the stability of chicken cystatin to temperature could be significantly improved. The $Asn_{106}$-glycosylated, modified chicken cystatin of the present invention, when for example added to surimi, has the desired inhibitory function even if said surimi is treated with several freezing-thawing cycles.

SUMMARY OF THE INVENTION

The present invention relates to a N-glycosylation-modified recombinant chicken cystatin, wherein $Asn_{106}$-$Ile_{108}$ in its amino acid sequence is modified to $Asn_{106}$-$Thr_{108}$. The $Asn_{106}$-glycosylated, modified recombinant chicken cystatin of the present invention, when for example added to surimi, is stable to temperature and has the desired function in the inhibition of thermal degradation of surimi even if said surimi is treated with several freezing-thawing cycles. The surimi is preferably derived from nemipterid, mackerel or cod.

In one aspect, the present invention relates to a nucleic acid molecule encoding the N-glycosylation-modified recombinant chicken cystatin of the present invention, wherein the triplet codon encoding the $108^{th}$ amino acid in the amino acid sequence of chicken cystatin is changed from AGT to TCA or its degenerate codons.

In another aspect, the present invention relates to an expression vector comprising the nucleic acid molecule encoding the N-glycosylation-modified recombinant chicken cystatin of the present invention. In a preferred embodiment, the expression vector is the expression vector pGAPZαC containing GAP promoter.

In yet another aspect, the present invention relates to a transformant harboring the expression vector. In a preferred embodiment, the host cell to be transformed is yeast. In a more preferred embodiment, the yeast is *Pichia pastoris*. In the most preferred embodiment, the yeast is *Pichia pastoris* strain X-33.

In yet another aspect, the present invention relates to a method for producing the N-glycosylation-modified recombinant chicken cystatin, which comprises the steps of culturing a nutritional medium with the yeast transformant of the present invention for producing the N-glycosylation-modified recombinant chicken cystatin, and recovering said N-glycosylation-modified recombinant chicken cystatin thus obtained.

In still yet another aspect, the present invention relates to a composition for inhibiting the thermal degradation and gel softening of surimi, comprising the N-glycosylation-modified recombinant chicken cystatin of the present invention and an acceptable expander. The expander may preferably be a compatible protein, starch or a combination thereof.

In still yet another aspect, the present invention relates to a method for inhibiting the thermal degradation and gel softening of surimi by using the composition, comprising adding said composition to surimi. In a preferred embodiment, 0.01 to 0.10 active units, preferably 0.02 to 0.05 active units, of the N-glycosylation-modified recombinant chicken cystatin of the present invention are added to 1 g of surimi.

DETAILED DESCRIPTION OF THE INVENTION

Figure 1:
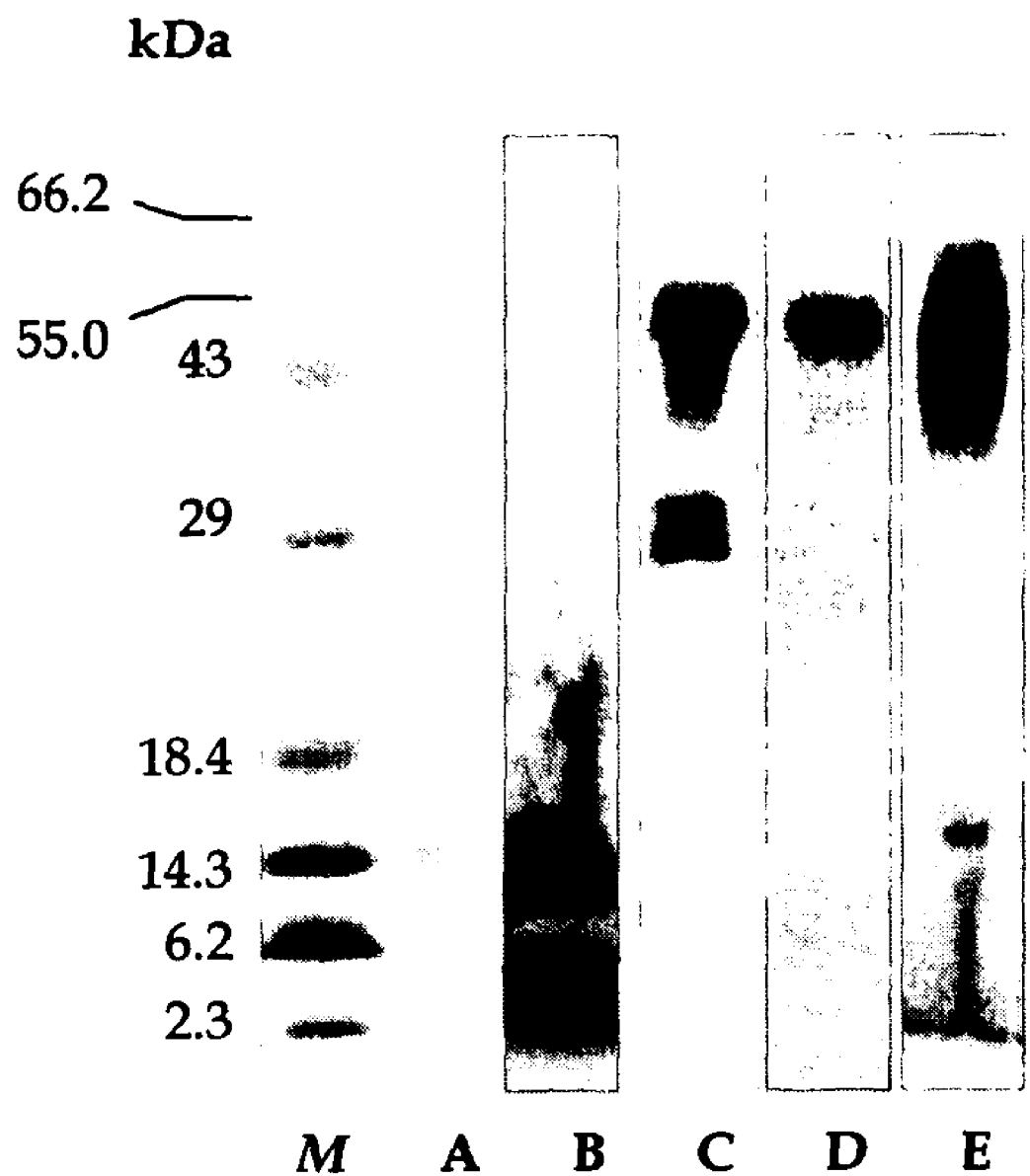
FIG. 1 illustrates SDS-PAGE and substrate SDS-PAGE (activity staining) of the $Asn_{106}$-glycosylation modified recombinant chicken cystatin using 15% of sodium dodecyl sulfate polyacrylamide electrophoresis, wherein lane M represents protein marker, lane A represents purified recombinant chicken cystatin, lanes B and E represent substrate (0.1% casein) SDS-PAGE of non- and $Asn_{106}$-glycosylated chicken cystatin, lane C represents glycosylated chicken cystatin after Sephacryl S-100 HR chromatography, and lane D represents purified glycosylated chicken cystatin.

The present invention relates to a novel glycosylated recombinant chicken cystatin, which can inhibit the thermal degradation and gel softening of fish meat or surimi. The glycosylated recombinant chicken cystatin of the present invention could be produced by employing site-directed mutagenesis and genetic engineering technique.

The site-directed glycosylation of proteins using yeast expression systems has been a new approach to enhance the molecular stability of recombinant protein produced (21, 28, 36). *Pichia pastoris*, a methylotrophic yeast, is an efficient system for the production of recombinant proteins with high expression level (14, 33). The GAP promoter gene has been characterized and can express recombinant proteins to high levels in *Pichia pastoris* (35).

For examining the effect of N-glycosylation on the freezing stability of recombinant chicken cystatin, the cDNAs coding chicken cystatin and its N-glycosylated mutant (Asn$_{106}$-Ile$_{108}$→Asn$_{106}$-Thr$_{108}$) were cloned into the pGAPZαC expression vector using the GAP as promoter and Zeocin as resistant agent, which pGAPZαC expression vectors obtained were then transformed into *Pichia pastoris* X-33 host cell. The papain-inhibition properties of the recombinant chicken cystatin and Asn$_{106}$-glycosylated mutant chicken cystatin were evaluated.

Materials and Methods

Strains: Cloning host: *Escherichia Coli* Top 10F'
Expression host: *Pichia pastoris* strain X-33

Plasmids: Cloning vector: pGEM-T Easy vector
Expression vector: pGAPZαC vector

Screening and Amplification of Cystatin cDNA from Chicken Lung mRNA

Total RNA from chicken lung was extracted using Trizol RNA extraction kit (Gibco BRL). The single strain cDNA, produced from RT-PCR, was used as a template. Based on the open reading frame from 128 to 478 for chicken cystatin, the oligonucleotide with 5'-CTCGAGAAAA GAGAGGCT-GAAGCTAGCGAGGACCGCTCCCGGCTCCTG GG and 5'-TCTAGATTACTGGCACTTGCTTTCCAGCAGTTT, were used as primers for the PCR reactions. Another antisense-primer, TCTAGATTACTGGCACTTGCTTTCCA GCAGTTTATTTGG, in which the $^{106}$Asn-Gln-$^{108}$Ile was replaced by Asn-Gln-Thr (shadowed) to create a glycosylation sequence, was used to substitute the 3'-primer in PCR reaction. Restriction sites at 5' end of the primers for XhoI and XbaI (underlined) were incorporated to facilitate subcloning of the product. Amplification was performed using proofreading polymerase (Gibco BRL) by polymerase chain reaction for 35 cycles with 30 sec. denaturation at 94° C.; 30 sec. annealing at 55° C. and 50 sec. extension at 68° C. in a DNA thermal cycler (GeneAmp PCR system 2400, Perkin Elmer, Norwalk, Conn.).

Construction of Chicken Cystatin Expression pGAPZαC Plasmid

The standard techniques of molecular cloning were performed mainly according to Sambrook et al. (32). The PCR product was cloned into pGEMT Easy vector (Promega) and then transformed into *E. coli* Top 10 F'. After blue/white selection and midi-preparation, the plasmid was digested with XhoI and XbaI and then ligated into pGAPZαC vector (Novagen).

Transformation and Selection in *Pichia pastoris* X-33 Expression Host

The pGAPZαC plasmid ligated with correct and/or glyco-modified chicken cystatin in-frame DNA sequence were digested with BglII in GAP promoter region to linearize the vector and then transformed into *Pichia pastoris* X-33, respectively, by using lithium chloride method (12). The colonies were selected by plating the transformants on YPDS agar plates (20 g/L tryptone, 10 g/L yeast extract, 20 g/L dextrose, 182.2 g/L sorbitol and 20 g/L agar) containing 100 μg/mL Zeocin. After at least 20 colonies for each treatment were produced, colonies that were integrated into their chromosome with the pGAPZαC-cystatin DNA and/or pGAPZαC-glyco-modified cystatin DNA and had the best expression quantity, were chosen.

Cultivation of *Pichia pastoris* X-33 Expression Host and Isolation of Recombinant Cystatin The chosen *Pichia pastoris* strains were cultivated with 5 mL YPDS broth (20 g/L tryptone, 10 g/L yeast extract, 20 g/L dextrose and 182.2 g/L sorbitol) containing 100 μg/mL Zeocin in a 50 mL flask using a shaking incubator (300 rpm) overnight at 30° C., and then 1 mL of the resulting culture was inoculated into 50 mL of fresh YPD broth (20 g/L tryptone, 10 g/L yeast extract and 20 g/L dextrose) in a 250 mL flask, which was then cultivated at 30° C. in a shaking incubator (300 rpm) for 4–5 days. The *Pichia pastoris* cells were excluded by 10 min. centrifugation at 3000×g. The supernatant was collected and subjected to the further purification.

Purification of Recombinant Chicken Cystatin

The recombinant chicken cystatin was purified by 40–60% saturated ammonium sulfate, Sephacryl S-100 HR and Superdex 75 chromatography, while Asn$_{106}$-glycosylation modified chicken cystatin was purified by Sephacryl S-100 HR, Con A Sepharose and FPLC Superose 12 chromatography.

Deglycosylation

The Asn$_{106}$-glycosylation modified chicken cystatin was first denatured by heating at 100° C. in the presence of 1% SDS for 10 min. The denatured Asn$_{106}$-glycosylation modified cystatin (0.1 mg) was then added to N-glycosidase F (5 units; BOEHRINGER MANNHEIM) in 20 mM sodium phosphate buffer (pH 7.2) containing 2% Triton X-100 and 0.2% SDS. The resulting sample was incubated at 37° C. overnight.

Sodium Dodecyl Sulfate Polyacrylamide Gel Electrophoresis (SDS-PAGE)

SDS-PAGE analysis was performed according to Laemmli (22) using a mini-gel system (SE 260 vertical gel unit, Hoefer). The concentration of polyacrylamide gel was 15%. After 30 min incubation with 1% β-mercaptoethanol at 50° C., samples were subjected to SDS-PAGE analysis. The staining and destaining were performed according to the method of Neuhoff et al. (30). Ovalbumin (43 kDa), carbonic anhydrase (29 kDa), β-lactoglobulin (18.4 kDa), lysozyme (14.3 kDa), bovine trypsin inhibitor (6.2 kDa), insulin (2.3 kDa) were used as markers.

Substrate SDS-PAGE

The substrate SDS-PAGE was performed according to El-Shamei et al. (17). A 12% of polyacrylamide gel containing 0.1% w/v casein was employed in this study. About 10 to 20 μg of sample protein was applied onto each well of the gels. After electrophoretical running, the gels were pre-washed with 2.5% Triton X-100 twice for 30 min. to remove SDS. The resulting gels were incubated with papain (0.01 mg/mL) in a 0.10 M phosphate buffer containing 2.0 mM cysteine and 1.0 mM EDTA (pH 6.0) at 37° C. for 60 min. The reaction was stopped by a staining solution (a mixture of 0.01% Coomassie brilliant blue, 40% methanol and 10% acetic acid). After destaining with 25% ethanol and 10% acetic acid, the visible intense blue bands were the active cystatin zones.

Freezing Stability

For investigating the influence of $Asn_{106}$-glycosylation on the freezing stability of chicken cystatin, the native, recombinant and its $Asn_{106}$-glycosylation modified cystatins were frozen at −20° C. in distilled water and then thawed at a 24-hour interval for 6 days. During each freezing-thawing process, the remaining activities of each cystatin were determined.

Assay of Enzyme Inhibitory Activity

Papain (EC 3.4.22.2) was used for the inhibition assessment. The inhibitory activity of chicken cystatin was assayed by measuring the remaining papain activity using Z-Phe-Arg-MCA as substrate (4). The enzyme, papain, in 0.2 M sodium phosphate buffer (pH 6.0) containing 4 mM cysteine and 2 mM EDTA with or without chicken cystatin were pre-incubated at 37° C. for 5 min. The enzyme reaction mixture (0.75 mL) comprised 5 μL enzyme, 0.25 ML 0.4 M sodium phosphate buffer (pH 6.0) containing 8 mM cysteine and 4 mM EDTA, 0.295 mL distilled water and 0.20 mL chicken cystatin. The reaction was started by adding 0.25 mL of 40 μM Z-Phe-Arg-MCA solution and stopped by adding 1.0 mL sodium acetate buffer containing 0.1 M sodium monochloroacetate (pH 4.3). The amount of liberated aminomethylcoumarin was determined by a spectrofluorometer at 350 nm for excitation and at 460 nm for emission. One unit of inhibitory activity was defined as the amount of chicken cystatin that could inhibit one unit of the proteolytic activity of papain, which was defined as the amount of papain that could hydrolyze Z-Phe-Arg-MCA and release 1 μmol aminomethylcoumarin within 1 min. at 37° C.

Kinetic Measurements

The inhibitory constants (Ki) were calculated by the method of Dixon (15). Fixed amounts of papain (a final concentration of 0.005, 0.01 and 0.02 nM for $Asn_{106}$-glycosylated, wild type and recombinant chicken cystatin, respectively) was incubated with appropriate amounts of inhibitors in a 0.1 M sodium phosphate buffer (pH 6.0) containing 2 mM cysteine, 1 mM EDTA and 0.1% Brij 35 at 40° C. for 3 min. The reaction was started by adding various concentrations of substrate (Z-Phe-Arg-MCA; 2, 4 or 10 μM), and the residual activities were measured (4). The inhibition constant (Ki) was calculated from the Dixon plots of 1/v vs. [I].

Protein Concentration Measurements

Protein concentrations were determined by the dye binding method using bovine serum albumin as the standard.

Results

After transforming *Pichia pastoris* X-33 expression host with the pGAPZαC chicken cystatin plasmid, the expression vector was integrated into genomic DNA due to the existence of GAP promoter sequence. Since the chicken cystatin gene was under control of GAP promoter, high level of the recombinant chicken cystatin was expressed and secreted into the broth by α-factor preprosequence during shaking cultivation. In both strains (with/without glycosylation modified mutants), the highest level of cystatin activities (about 6.33 units/mg) was observed after 2 days shaking cultivation. No significant difference in total cystatin activity between these 2 strains was obtained after 2 days shaking cultivation. Since no significant increase in cystatin activity was observed during the further cultivation, 2-day cultivation was used in this study.

The $Asn_{106}$-glycosylation modified *Pichia pastoris* strain, which was integrated into its chromosome with N-Q-$^{108}$I→N-Q-$^{108}$T mutant chicken cystatin gene downstrand of GAP promoter in its chromosome, expressed 2 recombinant cystatins (separated by Sephacryl S-100 HR gel filtration chromatography). One was a poly glycosylated protein with 40 degree of polymerization (DP), which amounted to about 50% of the total recombinant cystatins, while the other one was unglycosylated protein or glycoproteins with very low DP.

EXAMPLES

Example 1

Measurement of Molecular Weight

Figure 2:
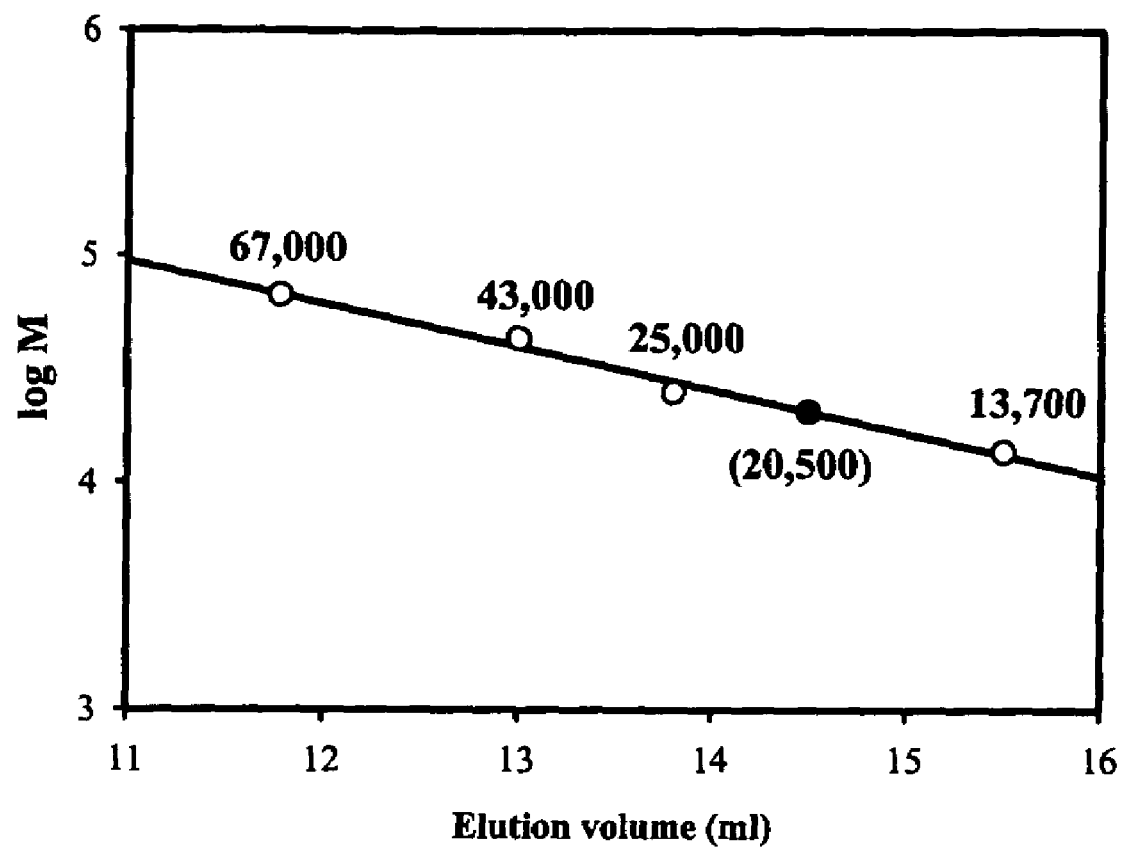
FIG. 2 illustrates the calibration curve for the determination of the molecular weight of purified $Asn_{106}$-glycosylation modified recombinant chicken cystatin using FPLC Superose 12 chromatography [○: markers; ●: purified Asn$_{106}$-glycosylation modified recombinant chicken cystatin].

The non-modified recombinant chicken cystatin was purified according to the previous study (13), while the $Asn_{106}$-glycosylated mutant chicken cystatin was purified to electrophoretical homogeneity by Sephacryl S-100 HR (FIG. 1, line C), Con A Sepharose (FIG. 1, line D) and Superose 12 chromatography (FIG. 1, line E). According to the N-terminal sequences analysis, the sequences of these 2 purified recombinant cystatins (with non- or glycosylation modification) were as predicted. The molecular weight (M) of the recombinant chicken cystatin (13) and its $Asn_{106}$-glycosylated mutant were 14 and 20.5 kDa (FIG. 2), respectively. Both $Asn_{106}$-glycosylated mutant chicken cystatin and its deglycosylated form were further confirmed by the substrate SDS-PAGE against papain (FIG. 1, lines B and E). As indicated in FIG. 1, the Coomassie brilliant blue stained unhydrolyzed casein band indicated the existence of papain inhibitor, which was the recombinant cystatins.

Example 2

Stability of the Native, Recombinant and $Asn_{106}$-glycosylated Recombinant Chicken Cystatin Against Freezing From the comparison of the residual activity of the native, recombinant and its $Asn_{106}$-glycosylation modified recombinant chicken cystatins during 6 freezing-thawing cycles (i.e. freezing at −20° C. for 14 h and thawing at 25° C. for 10 h), there was still 93% of the original activity remained in the $Asn_{106}$-glycosylation modified recombinant chicken cystatin, but only 65% and 63% remained in the non-modified recombinant and native cystatins, respectively (Table 1). This phenomenon suggested that the carbohydrate moiety on the $Asn_{106}$-glycosylation modified cystatin have a stabilizing effect on the cystatin.

TABLE 1

Stability of the native, recombinant and $Asn_{106}$-glycosylated recombinant chicken cystatin against freezing

| Time (day) | 0 | 1 | 2 | 3 | 4 | 5 | 6 |
|---|---|---|---|---|---|---|---|
| Native cystatin activity[1] (units) | 35.45 | 32.02 | 30.04 | 28.45 | 26.90 | 25.02 | 22.46 |
| Relative residual activity (%) | 100 | 90.32 | 84.73 | 80.23 | 75.87 | 70.56 | 63.35 |
| Recombinant cystatin activity[2] (units) | 147.23 | 138.52 | 132.76 | 127.60 | 101.75 | 100.73 | 95.36 |
| Relative residual activity (%) | 100 | 94.08 | 90.17 | 86.67 | 69.11 | 68.42 | 64.77 |
| Glycosylated cystatin activity[3] (units) | 156.32 | 153.02 | 153.45 | 150.36 | 150.76 | 146.35 | 146.01 |
| Relative residual activity (%) | 100 | 97.89 | 98.16 | 96.19 | 96.44 | 93.61 | 93.45 |

[1] The native chicken cystatin was purchased from Sigma Co Ltd., and purified again by Superose-12 chromatography.
[2,3] The recombinant chicken cystatin and its glycosylated form were expressed from pGAPZαC-cystatin transformed *Pichia pastoris* and purified by various steps.

Example 3

Thermal Stability of Recombinant and Glycosylated Recombinant Chicken Cystatin

Figure 3:
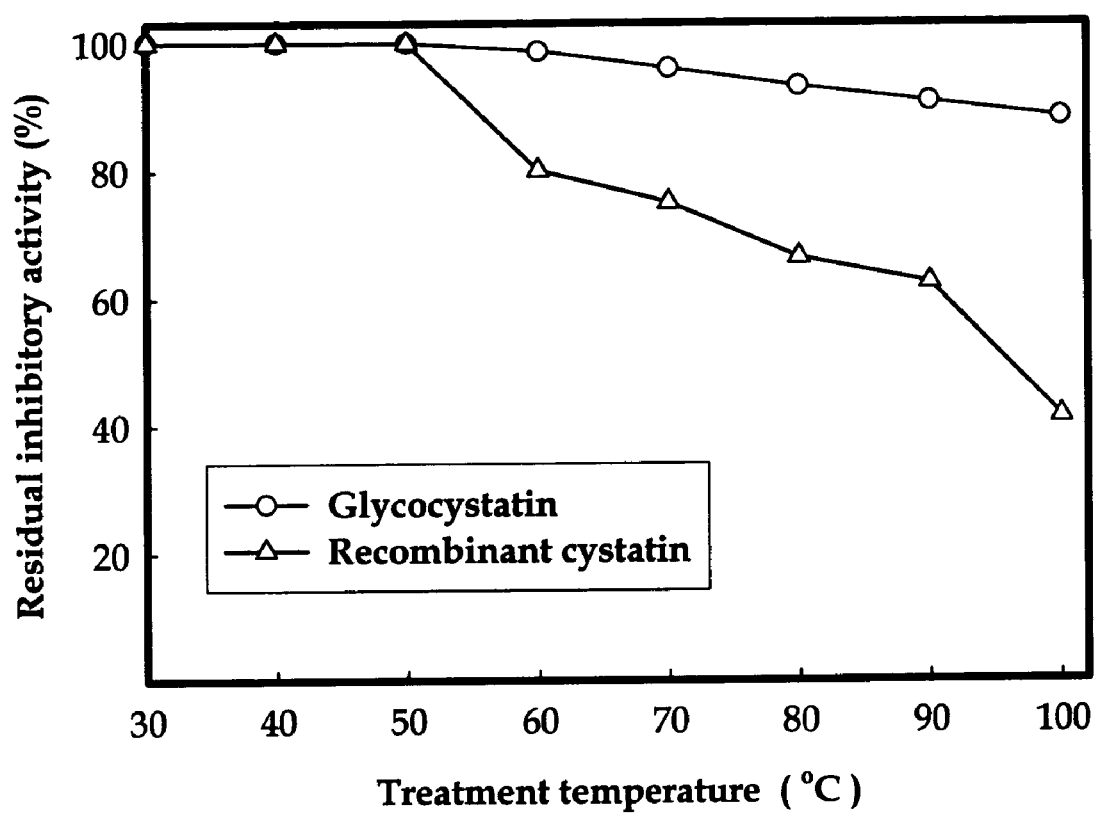
FIG. 3 illustrates comparison in the thermal stability of recombinant chicken cystatin and glycosylated recombinant chicken cystatin incubated at 30 to 100° C. for 30 min.

The recombinant and glycosylated recombinant chicken cystatins were dissolved in 50 mM Tris-HCl buffer (pH 7.5) respectively, and then were placed at 30, 40, 50, 60, 70, 80, 90 or 100° C. for 30 min. Thereafter, the inhibitory activity of said recombinant and glycosylated recombinant chicken cystatin was measured. The result was shown in FIG. 3, which indicated that the glycosylated recombinant chicken cystatin has a superior thermal stability to the non-glycosylated recombinant chicken cystatin in the range of 60 to 100° C.

Example 4

Use of the Recombinant and Glycosylated Recombinant Chicken Cystatin for the Storage of Surimi Preparation of Surimi Fresh loin of mackerel was minced, to which 4× volume of a cold alkaline solution containing 0.4% of $NaHCO_3$, 4× volume of cold water and 2× volume of 0.3% aqueous HCl were sequentially added for water-bleaching, wherein each water-breaching took 5 min. Thereafter, the resulting product was subjected to centrifugal dewatering. After the fish tendon was removed, 3% sucrose solution, 3% sorbitol and 0.2% polyphosphate containing 50% sodium polyphosphate and 50% sodium pyrophosphate were added to the product, which in turn was homogenized by a kneader mixer and was stored in a refrigerator at −40° C.

Figure 4:
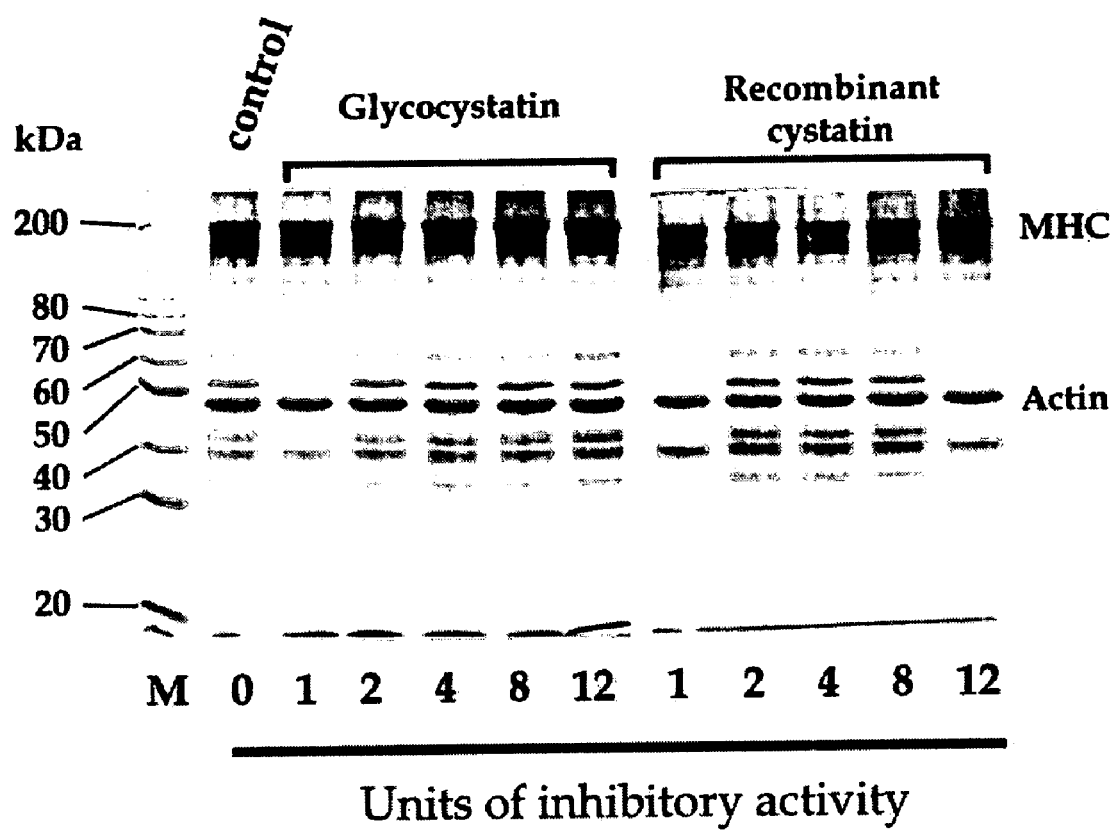
FIG. 4 illustrates SDS-PAGE analysis of mackerel surimi proteins, in which various treated-mackerel surimi gels were incubated at 50° C. for 90 min. and then at 95° C. for 10 min. and the dissolved proteins were electrophorectically running on a 10% polyacrylamide of SDS-PAGE, wherein line M represents a protein marker of 10 kDa ladder and MHC represents myosin heavy chain.

Effect of the Recombinant and Glycosylated Recombinant Chicken Cystatins on the Gel Softening of Fish Meat Jelly Product When mackerel surimi was kneaded in a 2.5% NaCl aqueous solution, a series of 0 to 12 active units of the recombinant or glycosylated recombinant chicken cystatin per 100 g of mackerel surimi were added (where the control did not contain any chicken cystatin), and the resulting products were kneaded homogeneously. The kneaded solutions were infused into casing materials with a diameter of 2.5 cm, and the products were then directly heated at 100° C. for 30 min., or were firstly put into a water bath of 50° C. for 2 hr and then were heated at 100° C. for 30 min. When the products were jelled, the jelled products were stored in a refrigerator at 4° C. for 12 hr. Thereafter, the strength of the jelled products was measured (wherein a 2.5 cm-high jelled sample was measured by an elastometer, which has a detection head with a diameter of 5 mm, at a detection velocity of 60 mm/min., and the strength (g×cm) of a jelled product was expressed by a product of breaking force (g)×deformation (mm)), and the jelled products were analyzed by electrophoresis (wherein 0.03 g of the jelled products was dissolved with heating at 50° C. in 2 ml of a buffer containing 2% SDS-8 M urea-2% β-Me-20 mM Tris-HCl, pH 8.0, and was analyzed by a non-continuous electrophoresis where the resolving gel was prepared by 10% acrylamide, the concentration of the stacking gel was 5%, the voltage for mini-gel electrophoresis was 100 V, and the resulting gel was stained by Coomassie brilliant blue G-250 and destained by 25% methanol and then dried). The results were shown in Table 2 and FIG. 4. It was found that there was no significant difference in the strength of the jelled products to which were added more than 2 active units of the recombinant or glycosylated recombinant chicken cystatin.

TABLE 2

Breaking force (g) and deformation (mm) of mackerel surimi supplemented with the recombinant and glycosylated recombinant chicken cystatins expressed from *Pichia pastoris* X-33 strain*

| | Recombinant cystatin | | Glycosylated recombinant cystatin | |
|---|---|---|---|---|
| Inhibitory activity (units)** | Breaking force (g) | Deformation (mm) | Breaking force (g) | Deformation (mm) |
| 0 | 277 ± 15.9[a] | 6.0 ± 0.31[a] | 277 ± 15.9[a] | 6.0 ± 0.31[a] |
| 1.0 | 355 ± 15.2[b] | 7.1 ± 0.36[b] | 344 ± 11.3[b] | 6.3 ± 0.20[a] |
| 2.0 | 432 ± 14.5[c] | 8.2 ± 0.42[c] | 380 ± 17.4[c] | 7.0 ± 0.24[b] |
| 4.0 | 480 ± 29.1[cd] | 8.9 ± 0.59[c] | 524 ± 22.9[d] | 8.6 ± 0.33[c] |
| 8.0 | 501 ± 27.5[d] | 9.1 ± 0.39[c] | 668 ± 28.4[e] | 10.2 ± 0.44[d] |
| 12.0 | 507 ± 17.2[d] | 9.0 ± 0.26[c] | 631 ± 37.1[e] | 10.0 ± 0.31[d] |

*Crude recombinant and glycosylated recombinant chicken cystatins obtained from culture broth of *Pichia pastoris* X-33 transformant was dialyzed against 20 mM phosphate buffer (pH 7.0).
**Values are the means of 10 determinations; values bearing unlike subscripts (a–e) in the same column are of significant difference (p < 0.05).

REFERENCES CITED (1) Anastasi, A.; Brown, M. A.; Kembhavi, A. A.; Nicklin, M. J. H.; Sayers, C. A.; Sunter, D. C.; Barrett, A. J. Cystatin, a protein inhibitor of cysteine proteinase. Improved purification from egg white, characterization, and detection in chicken serum. *Biochem. J.* 1983, 211, 129–138.

(2) Arima, H.; T. Kinoshita; H. R. Ibrahim; H. Azakami; A. Kato. Enhanced secretion of hydrophobic peptide fused lysozyme by the introduction of N-glycosylation signal and the disruption of calnexin gene in *Saccharomyces cerevisiae*. *FEBS Letters*, 1998, 440, 89–92.

(3) Auerswald, E. A.; G Genenger; I. Assfalg-Machleidt; W. Machleidt; R. A. Engh; H. Fritz. Recombinant chicken egg white cystatin variants of the QLVSG region. *Eur. J. Biochem.* 1992, 209, 837–845.

(4) Barrett, A. J.; H. Kirschke. Cathepsin B, cathepsins H, and cathepsins L. *Methods Enzymol.* 1981, 80, 535–562.

(5) Barrett, A. J. The cystatins: a new class of peptidase inhibitors. *Trends Biochem. Sci.* 1987, 12, 193–196.

(6) Barrett, A. J., N. D. Rawlings, M. E. Davies, W. Machleidt, G. Salvesen, and V. Turk. In *Proteinase Inhibitors*; Barrett, A. J. and Salvesen, G. eds. Elsevier Science Publishers BV, Amsterdam, 1986, pp: 515–569.

(7) Bjork, I.; K. Ylinenjarvi. Interaction of chicken cystatin with inactivated papains. *Biochem. J.* 1989, 260, 61–68.

(8) Bjork, I.; K. Ylinenjarvi. Interaction between chicken cystatin and the cysteine proteinases actinidin, chymopapain A, and ficin. *Biochemistry* 1990, 29, 1770–1776.

(9) Bjork, I.; E. Alriksson; K. Ylinenjarvi. Kinetics of binding of chicken cystatin to papain. *Biochemistry* 1989, 28, 1568–1573.

(10) Bode, W.; J. Brzin; V. Turk. Crystallization of chicken egg white cystatin, a low molecular weight protein inhibitor of cysteine proteinases, and preliminary X-ray diffraction data. *J. Mol. Biol.* 1985, 181, 331–332.

(11) Bode, W.; R. Engh; D. Musil; U. Thiele; R. Huber; A. Karshikov; J. Brzin; J. Kos; V. Turk. The 2.0 Å X-ray crystal structure of chicken egg white aystatin and its possible mode of interaction with cysteine proteinases. *EMBO J.* 1988, 7, 2593–2599.

(12) Brzobohaty, B.; L. Kovac. Factors enhancing genetic transformation of intact yeast cells modify cell wall porosity. *J. Gen. Microbiol.* 1986, 132, 3089–3093.

(13) Chen, G. H.; S. J. Tang; C. S. Chen; S. T. Jiang. High-level production of recombinant chicken cystatin by *Pichia pastoris* and its application in mackerel surimi. *J. Agric. Food Chem.* 2001, 49, 641–646.

(14) Cregg, J. M.; T. S. Vedvick; W. C. Raschke. Recent advances in the expression of foreign genes in *Pichia pastoris*. *Bio. Techn.* 1993, 11, 905–910.

(15) Dixon. M. The graphical determination of Km and Ki. *Biochem. J.* 1972, 129, 197–202.

(16) Elbein, A. D. The role of N-linked oligosaccharides in glycoproteins function. *TIBTECH* 1991, 9, 346–352.

(17) El-Shamei, Z.; J. W. Wu; N. F. Haard. Influence of wound injury on accumulation of proteinase inhibitors in leaf and stem tissues of two processing tomato cultivars. *J. Food Biochem.* 1996, 20, 155–171.

(18) Fossum, K.; J. R. Whitaker. Ficin and papain inhibitor from chicken egg white. *Arch. Biochem. Biophys.* 1968, 125, 367–375.

(19) Genenger, G.; S. Lenzen; R. Mentele; I. Assfalg-Machleidt; E. A. Auerswald. Recombinant Q53E- and Q53N-chicken egg white cystatin variants inhibit papain, actinidin and cathepsins B. *Biomed. Biochim. Acta.* 1991, 50, 621–625.

(20) Keilova, H.; V. Tomasek. Effect of papain inhibitor from chicken egg white on cathepsin B1. *Biochim. Biophys. Acta* 1974, 334, 179–186.

(21) Kwon, K. S.; M. H. Yu. Effect of glycosylation on the stability of $\alpha$1-antitrypsin toward urea denaturation and thermal deactivation. *Biochim. Biophys. Acta* 1997, 1335, 265–272.

(22) Laemmli, U. K. Cleavage of structural proteins during the assembly of the head bacteriophage T4. *Nature* (London) 1970, 277, 680–685.

(23) Lindahl, P.; E. Alriksson; H. Jornvall; I. Bjork. Interaction of the cysteine proteinase inhibitor chicken cystatin with papain. *Biochemistry* 1988, 27, 5074–5082.

(24) Lindahl, P.; M. Nycander, K. Ylinenjarvi; E. Pol; I. Bjork. Characterization by rapid-kinetic and equilibrium methods of the interaction between N-terminally truncated forms of chicken cystatin and the cysteine proteinases papain and actinidin. *Biochem. J.* 1992, 286, 165–171.

(25) Lloyd, R. C.; B. G Davis; J. B. Jones. Site-selective glycosylation of Subtilisin *Bacillus lentus* causes dramatic increases in esterase activity. *Bioorganic Medicinal Chem.* 2000, 8, 1537–1544.

(26) Machleidt, W.; U. Thiele; B. Laber; I. Assfalg-Machleidt; A. Esterl; G Wiegand; J. Kos; V. Turk; W. Bode. Machanism of inhibition of papain by chicken egg white cystatin. Inhibition constants of N-terminally truncated forms and cyanogen bromide fragments of the inhibitor. *FEBS Lett.* 1989, 243, 234–238.

(27) Machleidt, W.; U. Thiele; I. Assfalg-Machleidt; D. Forger; E. A. Auerswald. Molecular machanism of inhibition of cysteine proteinases by their protein inhibitors: Kinetic studies with natural and recombinant variants of cystatins and stefins. *Biomed. Biochim. Acta* 1991, 50, 613–620.

(28) Mer, G, H. Hietter, and J. F. Lefevre. Stabilization of proteins by glycosylation examined by NMR analysis of a fucosylated proteinase inhibitor. *Nature Structural Biol.* 1996, 3, 45–53.

(29) Nakamura, S.; H. Takasaki; K. Kobayashi; A. Kato. Hyper-glycosylation of hen egg white lysozyme in yeast. *J. Biol. Chem.* 1993, 268, 12706–12712.

(30) Neuhoff, V.; N. Arold; D. Taube; W. Ehrhardt. Improved staining of proteins in polyacrylaminde gel including isoelectric focusing gels with clear background at nanogram sensitivity using coomassie brilliant blue G-250 and R-250. *Electrophoresis* 1988, 9, 255–262.

(31) Nicklin, M. J.; A. J. Barrett. Inhibition of cysteine proteinases and dipeptidyl peptidase I by egg-white cystatin. *Biochem. J.* 1984, 223, 245–253.

(32) Sambrook, J.; E. F. Fritsch; T. Maniatis. In *Molecular cloning*, a laboratory manual, $2^{nd}$ ed., Vol. 1, Cold Spring Harbor Laboratory Press, Cold Spring Harbor, NY, 1989.

(33) Sreekrishna, K. Strategies for optimizing protein expression and secretion in the methylotrophic yeast *Pichia pastoris*. In *Industrial Microorganisms: Basic and Applied Molecular Genetics*. American Society for Microbiology, Washington, DC, 1993, pp. 119–126.

(34) Turk, V.; W. Bode. The cystatins: protein inhibitors of cysteine proteinases. *FEBS Lett.* 1991, 285, 213–219.

(35) Waterham, H. R.; M. E. Digan; P. J. Koutz; S. V. Lair; J. M. Cregg. Isolation of the *Pichia pastoris* glyceraldehyde-3-phosphate dehydrogenase gene and regulation and use of its promoter. *Gene* 1997, 186, 37–44.

(36) Zhu, A.; Z. K. Wang; R. Beavis. Structural studies of $\alpha$-N-acetylgalactosaminidase: effect of glycosylation on the level of expression, secretion efficiency, and enzyme activity. *Arch. Biochem. Biophys.* 1998, 352, 1–8.

What is claimed is:

1. An isolated N-glycosylation-modified recombinant chicken cystatin, characterized in that $Asn_{106}$-$Ile_{108}$ in its amino acid sequence is modified to $Asn_{106}$-$Thr_{108}$, and wherein the isolated N-glycosylated recombinant chicken cystatin has an improved stability in a freezing-thawing process and in a heating process.

2. The N-glycosylation-modified recombinant chicken cystatin of claim 1, which functions in the inhibition of thermal degradation and gel softening of surimi.

3. The N-glycosylation-modified recombinant chicken cystatin of claim 1, wherein said surimi is derived from nemipterid, mackerel or cod.

4. A composition for inhibiting the thermal degradation of surimi, comprising the N-glycosylation-modified recombinant chicken cystatin of claim 1 and an expander selected from the group consisting of a compatible protein, starch or a combination thereof.

5. A method of using the composition of claim 4 for inhibiting the thermal degradation of surimi, comprising adding the composition of claim 4 to surimi.

6. The method of claim 5, wherein the surimi is derived from nemipterid, mackerel or cod.

7. The method of claim 5 or 6, wherein 0.01 to 0.10 active units, of the N-glycosylation-modified recombinant chicken cystatin of claim 1 per 1 g of surimi is added.

8. The method of claim 7, wherein 0.02 to 0.05 active units of the N-glycosylation-modified recombinant chicken cystatin of claim 1 per 1 g of surimi is added.

* * * * *

SEQUENCE LISTING

<160> NUMBER OF SEQ ID NOS: 3

<210> SEQ ID NO 1
<211> LENGTH: 50
<212> TYPE: DNA
<213> ORGANISM: Artificial Sequence
<220> FEATURE:
<223> OTHER INFORMATION: Oligonucleotide primer

<400> SEQUENCE: 1
ctcgagaaaa gagaggctga agctagcgag gaccgctccc ggctcctggg          50

<210> SEQ ID NO 2
<211> LENGTH: 33
<212> TYPE: DNA
<213> ORGANISM: Artificial Sequence
<220> FEATURE:
<223> OTHER INFORMATION: Oligonucleotide primer

<400> SEQUENCE: 2
tctagattac tggcacttgc tttccagcag ttt                            33

<210> SEQ ID NO 3
<211> LENGTH: 40
<212> TYPE: DNA
<213> ORGANISM: Artificial Sequence
<220> FEATURE:
<223> OTHER INFORMATION: Antisense primer

<400> SEQUENCE: 3
tctagattac tggcacttgc tttccagcag tttagtttgg                     40